United States Patent [19]
Baralt et al.

[11] Patent Number: 6,054,629
[45] Date of Patent: Apr. 25, 2000

[54] METHOD OF ISOMERIZING ALPHA-OLEFINS TO LINEAR INTERNAL OLEFINS WITH MINIMAL SKELETAL ISOMERIZATION USING NICKEL SUPPORTED ON SILICA/ALUMINA CATALYSTS

[75] Inventors: Eduardo J. Baralt, Houston; Amy C. King, Humble; Carol E. King, Houston, all of Tex.

[73] Assignee: Chevron Chemical Company LLC, San Francisco, Calif.

[21] Appl. No.: 09/115,815

[22] Filed: Jul. 15, 1998

[51] Int. Cl.[7] .................................................... C07C 5/23
[52] U.S. Cl. ................................. 585/670; 585/664
[58] Field of Search ....................... 585/664, 670

[56] References Cited

U.S. PATENT DOCUMENTS

| | | | |
|---|---|---|---|
| 3,723,556 | 3/1973 | Wilhelm | 585/670 |
| 3,793,393 | 2/1974 | Neal | 585/670 |
| 3,821,123 | 6/1974 | Germanas et al. | 585/670 |

*Primary Examiner*—Walter D. Griffin
*Assistant Examiner*—Tam M. Nguyen
*Attorney, Agent, or Firm*—J. W. Ambrosius; W. B. Haymond; W. K. Turner

[57] ABSTRACT

The present invention relates to a method of using nickel alumina catalyst to isomerize linear alpha olefins substantially completely to linear internal olefins with no significant increase in branch internal olefin content.

9 Claims, No Drawings

METHOD OF ISOMERIZING ALPHA-OLEFINS TO LINEAR INTERNAL OLEFINS WITH MINIMAL SKELETAL ISOMERIZATION USING NICKEL SUPPORTED ON SILICA/ALUMINA CATALYSTS

FIELD OF THE INVENTION

The present invention relates to a method of isomerizing alpha-olefins to linear internal olefins with minimal skeletal isomerization.

BACKGROUND OF THE INVENTION

Olefins, either alpha-olefins or internal olefins, and either linear or branched, have been used in drilling fluids used in the drilling of subterranean oil and gas wells as well as other drilling fluid applications and drilling procedures.

Workers in the olefins field are searching for better, more efficient, less costly ways to isomerize alpha-olefins to linear internal olefins without increasing branched olefin content.

Several methods are known which achieve isomerization of olefins but are not successful in minimizing branched olefin content and/or have other disadvantages. For example, it is known that such synthetic hydrocarbons can be prepared by oligomerizing one or more olefinic monomers, such as those monomers having a chain length of from $C_2$ to $C_{14}$.

A known method for Isomerizing olefins utilizes platinum supported on a SAPO-11 molecular sieve catalyst. In Gee et al. (U.S. Pat. No. 5,589,442), incorporated herein by reference, the platinum/SAPO-11 catalyst is used to partially isomerize a feed containing $C_{14}$ to $C_{18}$ olefins, preferably linear olefins, and more preferably normal alpha-olefins. The product is a mixture of linear and branched olefins, with predominately internal olefins. This catalyst is not effective to achieve a mixture which is essentially completely linear internal olefins. Rather, a significant portion of the product is branched and/or alpha-olefins.

Other methods are known which have similar disadvantages. For example, Becker et al. (German Patent No. 4139552) teach isomerization of N-alkenes to iso-alkenes using microporous aluminophosphate catalyst with inert gas hydrogen and alkene-containing hydrocarbon mixture.

Khare et al. (U.S. Pat. No. 5,304,696) teach double bond isomerization of olefinic compounds by contacting an olefinic compound and a sulfated zirconia catalyst.

Heckelsberg (U.S. Pat. No. 3,823,572) teaches converting an olefin hydrocarbon, such as propylene and/or butene, to at least one other olefin hydrocarbon, such as isoamylenes, in a catalytic conversion process utilizing simultaneous or sequential contacting of an olefin reaction catalyst and a skeletal isomerization catalyst.

Suzukamo et al. (Japanese Patent No. 01019027) teach isomerizing olefins into stable internal olefins in the presence of a solid base catalyst prepared by heating at 200–450 degrees in an inert gas an alkali metal hydride and $Al_2O_3$ pretreated with an alkali metal carbonate or aluminate.

Slaugh (German Patent No. 2336138) teaches double bond isomerization of normal alkenes at 20–100 degrees over a catalyst composed of a K salt on an activated alumina carrier (pretreated 2–16 hours at 350–700 degrees in a nonoxidizing atmosphere).

The present Applicants have found that nickel supported on a silica/alumina catalyst can be used for the almost complete isomerization of alpha-olefins to linear internal olefins with minimal formation of branched olefins. Such a finding is a major development in the olefins field, because the nickel supported on a silica/alumina catalyst is an economical alternative to previously used catalysts and is actually more effective than prior art catalysts used with this reaction.

SUMMARY OF THE INVENTION

In one embodiment, the present invention relates to a method of using nickel supported on a silica/alumina catalyst to produce a mixture of linear internal olefins from an alpha olefin feed comprising heating the feed in the presence of said catalyst.

In a preferred embodiment of the present invention, the temperature of the heating step in the above method is from 100 to 250° C.

In another preferred embodiment of the present invention, the heating step in the above method is either a batch or continuous flow reaction.

In yet another preferred embodiment of the present invention, the mixture in the above method is at least 80 weight % linear internal olefins.

In still another embodiment of the present invention, the present invention relates to a method of isomerizing $C_4$ to $C_{40}$ alpha olefins to a mixture comprising at least 80 weight % linear internal olefins comprising heating $C_4$ to $C_{40}$ alpha olefins in the presence of nickel supported on a silica/alumina catalyst.

In a preferred embodiment of the present invention, the mixture in the above method comprises at least 90 weight % linear internal olefins.

In a more preferred embodiment of the present invention, the mixture in the above method comprises less than 5 weight % catalyst-caused skeletal isomers.

In a yet more preferred embodiment of the present invention, the mixture in the above method comprises less than 5 weight % residual alpha olefin.

In yet another preferred embodiment of the present invention, the heating step in the above method is conducted at a temperature between 100 and 250° C.

DETAILED DESCRIPTION OF THE INVENTION

The present invention provides a method of producing linear, internal olefins from alpha-olefins using nickel/aluminum catalysts.

EXAMPLES

The invention will be further illustrated by the following examples, which set forth particularly advantageous method embodiments. While the Examples are provided to illustrate the present invention, they are not intended to limit it.

Example 1

Linear $C_{16}$ alpha olefin is contacted with 100 grams of a nickel catalyst on a silica/alumina catalyst in a continuous flow reactor to produce linear internal olefins without significantly increasing the branch olefin content. Weight Hourly Space Velocity (WHSV) is from 0.9 to 1.5. The temperature is from 100 to 250° C. Table 1 is a summary of the data obtained in a continuous flow reactor.

TABLE 1

| WHSV | Temp (° C.) | Run duration (hours) | GC % Skeletal isomerization* | IR % Alpha |
|---|---|---|---|---|
| 1.5 | 200 | 215 | 0.294 | 4.96 |
| 1.5 | 200 | 241 | 1.59 | 3.34 |
| 1.5 | 200 | 244 | 1.27 | 3.29 |
| 1.5 | 200 | 264 | 1.68 | 2.77 |
| 1.5 | 200 | 292.5 | 1.88 | 2.98 |
| 1.5 | 200 | 316 | 1.69 | 2.83 |
| 1.5 | 200 | 343 | 2.67 | 1.99 |
| 1.5 | 200 | 366 | 4.5 | 2 |
| 1.5 | 200 | 419 | 1.41 | 3.33 |
| 1.5 | 200 | 534.5 | 2.8 | 2.01 |
| 1.5 | 200 | 581.5 | 2.74 | 2.04 |
| 1.3 | 185 | 614.5 | N/A | 11 |
| 0.9 | 185 | 678.5 | 0.21 | 3.73 |
| 0.9 | 185 | 705.5 | 0 | 3.97 |
| 0.9 | 185 | 749.5 | 0.06 | 3.65 |

*Weight percentage of skeletal isomerization introduced during isomerization.

Example 2

In comparative batch experiments, a catalyst was combined with 100 ml of $C_{16}$ alpha-olefin in a 250 ml round bottom flask. The reaction mixture was heated to the working temperature and stirred for the appropriate reaction time. The results are shown in Table 2 below. In Experiments 1–3, Chevron LISO, a nickel on alumina catalyst, is used which is described further in Example 4. In Experiment 4, HTC-500, a solid nickel on alumina catalyst from Crosfield, is used. In Experiment 5, Ni-3288, a solid nickel on silica/alumina catalyst from Engelhard, is used. In Experiment 6, SAPO-11, a molecular sieve, is used.

TABLE 2

| Exp | Catalyst | Amt. (grams) | Time (hours) | Temp (° C.) | % Alpha | % Skeletal isomerization* |
|---|---|---|---|---|---|---|
| 0 | Standard 1-$C_{16}$ | 0 | 0 | N/A | 93 | 0 |
| 1 | Chevron LISO | 6 | 2 | 220 | 1.1 | 2.65 |
| 2 | Chevron LISO | 6 | 2 | 130 | 93 | 0 |
| 3 | Chevron LISO | 6 | 2 | 200 | 12.8 | 0.4 |
| 4 | HTC-500 | 3 | 4 | 200 | 93 | 0 |
| 5 | Ni-3288 | 3 | 4 | 200 | 92 | 0 |
| 6 | SAPO-11 | 3 | 4 | 170 | 1 | 17.3 |

*Weight percentage of skeletal isomerization introduced during isomerization.

Example 3

Linear $C_{18}$ alpha olefin is contacted with a nickel on silica/alumina catalyst in a continuous flow reactor to produce linear internal olefins without significantly increasing the branch olefin content. Weight Hourly Space Velocity (WHSV) is from 0.72 to 1.52. The temperature is from 100 to 250° C. Table 3 is a summary of the data obtained in a continuous flow reactor.

TABLE 3

Isomerized $C_{18}=$ Catalyst: 100 g Chevron LISO catalyst

| Run time (days) | Temp. | WHSV | % Int. | % Alpha | % Vinyl | C#$C_{36}$ |
|---|---|---|---|---|---|---|
| 1 | 195° C. | 0.78 | 97.56 | 0.52 | 1.92 | 3.72 |
| 2 | 195° C. | 0.72 | 98.01 | 0.55 | 1.44 | 3.76 |
| 3 | 195° C. | 1.32 | 97.69 | 0.98 | 1.33 | 2.41 |
| 4 | 195° C. | 0.90 | 98.08 | 0.72 | 1.20 | 2.66 |
| 5 | 190° C. | 0.78 | 97.49 | 1.01 | 1.49 | 1.96 |
| 8 | 190° C. | 0.72 | 97.57 | 0.86 | 1.57 | 2.06 |
| 9 | 180° C. | 1.60 | 89.91 | 9.24 | 0.85 | 1.03 |
| 10 | 183° C. | 1.20 | 97.22 | 1.54 | 1.24 | 1.56 |
| 11 | 180° C. | | 97.01 | 1.25 | 1.74 | 1.25 |
| 14 | 175° C. | | 97.19 | 1.39 | 1.42 | 1.42 |
| 15 | 170° C. | 1.28 | 97.03 | 1.90 | 1.07 | 0.98 |
| 16 | 170° C. | 1.16 | 96.79 | 2.12 | 1.10 | |
| 18 | 170° C. | | 94.71 | 4.22 | 1.06 | 0.85 |
| 19 | 170° C. | 1.47 | 89.01 | 10.22 | 0.77 | 0.55 |
| 21 | 170° C. | 1.40 | 88.70 | 10.48 | 0.84 | 0.51 |
| 22 | 175° C. | 1.20 | 86.30 | 13.10 | 0.59 | |
| 25 | 180° C. | | 96.18 | 2.46 | 1.36 | 0.97 |
| 26 | 180° C. | 1.43 | 91.87 | 7.22 | 0.90 | 0.82 |
| 27 | 185° C. | | 95.89 | 3.09 | 1.02 | |
| 28 | 185° C. | | 96.06 | 2.79 | 1.16 | |
| 29 | 185° C. | | 95.65 | 3.23 | 1.12 | |

Example 4

Preparation of the Chevron LISO Nickel on Silica/Alumina Catalyst

The catalyst is a Nickel promoted pentasil zeolite having an alumina binder. The pentasil zeolite is prepared according to the teachings of U.S. Pat. No. 3,702,886, "Crystalline Zeolite ZSM-5 and Method of Preparing the Same", R. Argauer and G. Landolt, assignors to Mobil Oil Corporation. The preferred composition is a zeolite having a $SiO_2/Al_2O_3$ molar ratio of 80 to 90. The zeolite is calcined to remove the organic template, and then ion-exchanged to the H-form (acid) by use of strong mineral acid such as Hydrogen Chloride (HCl) to reduce the Sodium (Na) content to less than 100 ppm by weight. The zeolite is then compounded with a low sodium alumina powder and formed into an extrudate, sphere, pellet or tablet. A mixture of 70–80% zeolite dry weight basis (preferably 75%) and 20–30% dry weight basis alumina powder (preferably 25%) is intensively mixed in a blender, followed by addition of water, optionally containing 2–5% of nitric acid for peptization of the alumina. This mixture is then extruded, pelletized, spheroidized, or tabletted by methods known to those skilled in the art. The preferred form is an extrudate, which may be and by use of an extruder of the type manufactured by Bonnet Company. The extrudates are dried and calcined at 450–550° C. in a box, rotary, or belt calciner. The calcined extrudates are then impregnated with a nickel salt solution to yield a nickel monoxide content of 1–10% by weight of the final catalyst, and calcined at a minimum of 450° C.

The above procedure results in a catalyst having the following properties:

Chemical Properties of LISO Catalyst

| Chemical Comp. of LISO Catalyst | Weight % Basis at 537.8° C. |
|---|---|
| Ni | 6.0 ± 1.0 |
| $SiO_2$ | 66.0 ± 1.0 |
| $Al_2O_3$ | 26.4 ± 1.0 |
| Na, ppm | ≦150 |
| Fe, ppm | ≦500 |
| Mg, ppm | ≦500 |
| Ca, ppm | ≦500 |
| C, ppm | ≦300 |

Physical Properties of LISO Catalyst

| Form | Extrudate |
|---|---|
| Size | 1/16", 1/10" CDS, 1/8" |
| Compacted Bulk Density, lbs/ft$^3$ | 42 ± 3 |
| Crush Strength, lbs./mm | ≧2.0 |
| BET Surface Area, m$^2$/g | ≧275 |
| Pore Volume (Hg), cm$^3$/g | 0.30–0.45 |
| Attrition Resistance (ASTM) | ≦2.0 |

While the present invention has been described with reference to specific embodiments, this application is intended to cover those various changes and those may make those substitutions skilled in the art without departing from the spirit and scope of the appended claims.

What is claimed is:

1. A method for isomerizing alpha olefins to produce a mixture of linear internal olefins which comprises heating the alpha olefins in the presence of a pentisil zeolite which contains only one isomerization promoter consisting of between 1 weight percent and 10 weight percent of nickel monoxide.

2. The method of claim 1 wherein the temperature of the heating steps is from 100 to 250° C.

3. The method of claim 1 wherein the heating step is either a batch or continuous flow reaction.

4. The method of claim 1 wherein the product mixture is at least 80 weight % linear internal olefins.

5. A method of isomerizing $C_4$ to $C_{40}$ alpha olefins to a mixture comprising at least 80 weight % linear internal olefins comprising heating $C_4$ to $C_{40}$ alpha olefins in the presence of ZSM-5 zeolite which contains only one isomerization promoter consisting of between 1 weight percent and 10 weight percent of nickel monoxide.

6. A method according to claim 5 wherein the mixture comprises at least 90 weight % linear internal olefins.

7. A method according to claim 5 wherein the mixture comprises less than 5 weight % catalyst-caused skeletal isomers.

8. A method according to claim 7 wherein the mixture comprises less than 5 weight % residual alpha olefin.

9. The method according to claim 5 wherein the heating step is conducted at a temperature between 100 and 250° C.

* * * * *